(12) United States Patent
Wimberger-Friedl et al.

(10) Patent No.: US 9,470,609 B2
(45) Date of Patent: Oct. 18, 2016

(54) PREPARATION OF THIN LAYERS OF A FLUID CONTAINING CELLS FOR ANALYSIS

(75) Inventors: Reinhold Wimberger-Friedl, Eindhoven (NL); Nicolaas Petrus Willard, Eindhoven (NL); Ivo Godfried Jozef Camps, Eindhoven (NL); Markus Laubscher, Eindhoven (NL); Emiel Peeters, Eindhoven (NL); Oana Mihaela Piciu, Eindhoven (NL)

(73) Assignee: Koninklijke Philips N. V., Eindhoven (NL)

( * ) Notice: Subject to any disclaimer, the term of this patent is extended or adjusted under 35 U.S.C. 154(b) by 1252 days.

(21) Appl. No.: 13/263,446

(22) PCT Filed: Apr. 9, 2010

(86) PCT No.: PCT/IB2010/051537
§ 371 (c)(1),
(2), (4) Date: Oct. 7, 2011

(87) PCT Pub. No.: WO2010/116341
PCT Pub. Date: Oct. 14, 2010

(65) Prior Publication Data
US 2012/0225446 A1 Sep. 6, 2012

(30) Foreign Application Priority Data
Apr. 9, 2009 (EP) ..................................... 09305306

(51) Int. Cl.
*G01N 33/00* (2006.01)
*G01N 1/28* (2006.01)
(Continued)

(52) U.S. Cl.
CPC ........... *G01N 1/2813* (2013.01); *B01L 3/5025* (2013.01); *G01N 21/03* (2013.01); *B01L 2200/026* (2013.01); *B01L 2200/0642* (2013.01); *B01L 2300/0816* (2013.01); *B01L 2300/0829* (2013.01); *B01L 2300/0864* (2013.01); *B01L 2400/0688* (2013.01); *G01N 2021/0346* (2013.01); *Y10T 29/49* (2015.01)

(58) Field of Classification Search
None
See application file for complete search history.

(56) References Cited

U.S. PATENT DOCUMENTS 4,088,448 A 5/1978 Lilja et al.
4,790,640 A 12/1988 Nason
(Continued)

FOREIGN PATENT DOCUMENTS

JP 2005265634 A 9/2005
JP 2006101708 A 4/2006
(Continued)

*Primary Examiner* — Jill Warden
*Assistant Examiner* — Brittany Fisher (57) ABSTRACT

Apparatus for producing thin layers of a fluid sample for analysis, has a two dimensional array of analysis chambers (45), and a branching pattern of entry channels (25) coupled to the array to enable the analysis chambers to be filled in parallel. The analysis chambers are planar with a height less than that of the entry channels so as to produce the thin layers when filled with the fluid sample. The array enables more spacers between chambers in a given area, so that variations in height of the chambers can be reduced, while still enabling fast filling of the chambers. The analysis chambers can be suitable for capillary filling by a specified fluid sample such as blood. A pattern of exit channels (35) can be coupled to the array. The entry and exit channels can form comb patterns, fingers of the comb patterns being interdigitated, and the analysis chambers being arranged between the interdigitated fingers of the comb patterns.

12 Claims, 4 Drawing Sheets

(51) Int. Cl.
*B01L 3/00* (2006.01)
*G01N 21/03* (2006.01)

(56) References Cited

U.S. PATENT DOCUMENTS

| | | | |
|---|---|---|---|
| 5,100,620 A | 3/1992 | Brenneman | |
| 5,470,751 A | 11/1995 | Sakata et al. | |
| 5,837,200 A | 11/1998 | Diessel et al. | |
| 6,165,739 A | 12/2000 | Clatch | |
| 6,599,475 B1 | 7/2003 | Berndt et al. | |
| 6,819,408 B1* | 11/2004 | Scrivens et al. | 356/39 |
| 2002/0106786 A1 | 8/2002 | Carvalho et al. | |
| 2002/0160518 A1 | 10/2002 | Hayenga et al. | |
| 2003/0152927 A1 | 8/2003 | Jakobsen et al. | |
| 2004/0072278 A1* | 4/2004 | Chou et al. | 435/29 |
| 2006/0141607 A1 | 6/2006 | Wikswo et al. | |
| 2008/0297169 A1* | 12/2008 | Greenquist et al. | 324/600 |
| 2009/0149345 A1 | 6/2009 | Nishi et al. | |

FOREIGN PATENT DOCUMENTS

| | | |
|---|---|---|
| JP | 2007171144 A | 7/2007 |
| JP | 2008039584 A | 2/2008 |
| JP | 2008233003 A | 10/2008 |
| WO | WO9205243 | 4/1992 |

* cited by examiner

PREPARATION OF THIN LAYERS OF A FLUID CONTAINING CELLS FOR ANALYSIS

FIELD OF THE INVENTION

This invention relates to apparatus and methods for preparing thin layers of fluid for analysis and to systems and methods for analyzing such thin layers, especially to methods and apparatus for automated analysis of samples in a cartridge. The present invention particularly relates to apparatus and methods for preparing thin layers, especially monolayers of cells such as red blood cells, e.g. not having overlapping red blood cells, for analysis and to systems and methods for analyzing such thin layers or monolayers of cells, especially to methods and apparatus for automated analysis of samples in a cartridge.

BACKGROUND OF THE INVENTION

Cell based analysis can be carried out by staining cells with a specific reagent and inspecting the cell population in a microscope. For imaging-based cell diagnostics, e.g. using a microscope, a camera and a software application for image analysis and diagnosis, it is important to create a monolayer of separated cells to avoid misinterpretations due to cell overlap. One such method has been known for many years and involves scraping a volume of the relevant fluid, e.g. blood, over a glass slide by hand (smear). For an integrated closed cartridge this process cannot be used. Instead capillary filling of narrow channels can be used.

It is known from U.S. Pat. No. 6,599,475-B1 to provide a plastic optical cuvette for creating a thin monolayer of red blood cells for microscopic analysis. A number of compartments are provided connected in series and separated by separating walls. These walls each allow flow of only some of the red blood cells, to achieve red blood cell dilution, so that a monolayer of isolated red blood cells is achieved in the last of the compartments. To achieve a constant thickness across the whole cuvette, the separating walls have weld features and a transparent lid is welded to the top. A compartment may have dimensions 600×600×3 micrometers. For applications like analysis of blood samples for the malaria parasite, a large volume of blood needs to be analysed to achieve the required detection limit. With layer thicknesses of the order of the dimensions of red blood cells (5 μm) this means that large surface areas (square cms) need to be inspected.

U.S. Pat. No. 6,165,739-A1 describes a glass or plastic slide for laser cytometry having a number of capillary gap chambers. A fluid sample can enter all chambers simultaneously from a reservoir. A different reactant is provided in each chamber to enable multiple simultaneous reactions.

SUMMARY OF THE INVENTION

An object of the invention is to provide alternative apparatus and methods for preparing thin layers of fluid for analysis and/or systems and methods for analyzing such thin layers, in particular to apparatus and for automated analysis of samples in a cartridge. It is a separate object of the present invention to provide apparatus and methods for preparing layers from fluids having cells in which the layers have monolayers of cells such as red blood cells, e.g. not having overlapping cells such as red blood cells, for analysis and to systems and methods for analyzing such monolayers of cells, especially to methods and apparatus for automated analysis of samples in a cartridge.

According to a first aspect, the invention provides:
Apparatus for producing thin layers of a fluid sample or for producing layers of a fluid containing cells, especially red blood cells, each layer having a monolayer of cells, especially red blood cells for analysis, the apparatus having a two dimensional array of analysis chambers, and a branching pattern of entry channels coupled to each of the analysis chambers in the array to enable the analysis chambers to be filled in parallel, the analysis chambers each having a substantially planar shape having a height less than that of the entry channels so as to produce the thin layers of the fluid sample or to produce the layers of a fluid containing cells, especially red blood cells, each layer having a monolayer of cells when the chambers are filled with the fluid sample.

By providing a two dimensional array of analysis chambers, and a pattern of entry channels to couple the chambers in parallel, more spacers between chambers can be provided in a given area, so that variations in height of the chambers can be reduced, while still enabling fast filling of the chambers.

Embodiments can have any additional features, and some such additional features are described in more detail below.

The apparatus according to the invention preferably further comprising an additional zone (55) between the entry channels (25) and analysis chambers (45), wherein the height of this zone is less than the entry channels (25) and more than the analysis chambers (45). In a more preferred embodiment, the height of the additional zone (55) is below 6 micron. The advantage of this additional zone (55) is that red blood cells with mature parasite will be enriched in this area. This will prevent white blood cells being concentrated at the rim of the scan area thus obstructing proper analysis.

The chambers and/or channels can have dimensions suitable for capillary filling by a specified fluid sample, e.g. a fluid containing cells especially blood. In embodiments of the present invention, dimensions suitable for capillary filling can be defined by capillary filling by a standard aqueous solution such as PBS or pure water for example. This means that channels that are suitable for and capable of capillary filling in accordance with the present invention, fill by capillary action using PBS (Phosphate buffered saline) as a standard, e.g. at standard temperature and pressure, or optionally for example with pure water at standard temperature and pressure.

Devices of the present invention preferably have a number of chambers combined with the use of comb-like or fractal filling and venting channels. In a preferred embodiment the total surface will be 20 mm² and the field of view 0.2×0.2=0.04 mm², which means 500 reaction chambers. A number of chambers for any of the embodiments of the present invention can be between 1 and 1000 chambers. Preferably, the total area of each of the analysis chambers being between 100 and 2000 mm² and/or the height of the analysis chambers being between 1 and 10 μm.

The apparatus has a pattern of exit channels with one or more exit channels coupled to each of the analysis chambers. The patterns of the entry and exit channels can each comprise a comb pattern, fingers of the comb patterns being interdigitated, and the analysis chambers being arranged between the interdigitated fingers of the comb patterns. Another aspect of the present invention is the introduction of fluidic stops at or adjacent to the exit channels or vents. By introducing sharp transitions in the channel wall such as to change the width of the channel in all directions, the contact line of the liquid and the wall becomes frustrated since the angle cannot be changed abruptly. This leads to a hesitation of the fluid followed by so-called contact line pinning. The meniscus becomes frozen at the surface. If the channel is quadratic and has 4 walls then the widening is done at all 4 walls at the same spot the pinning can be very stable. The wall transitions preferably increase the angle count, i.e. they can be preferably stepwise expansions. With fluids like blood evaporation of water can lead to permanent pinning by vitrification of the liquid at the meniscus.

The apparatus may have a single sample port suitable for receiving a fluid sample such as a fluid sample containing cells, e.g. blood, the sample port being fluidly connected to branching pattern of entry channels so that these fill by capillary action. The preferred minimal height of the entry canals is 17 micrometer as this will prevent clogging by large white blood cells, monocytes.

The channels including the entry but excluding exit channels, and/or the chambers preferably have a hydrophilic surface. This hydrophilic surface may be a property of a material from which these are made or may be induced by other means, e.g. by corona discharge, by plasma discharge or by being coated with a hydrophilic coating. The venting channels are preferably arranged to provide a fluidic stop for liquids while allowing gas to pass, e.g. by making them have hydrophobic surfaces or by changing the width of the venting channels at one point to pin the liquid at the width change point. At least one of the surfaces above or below the chambers is preferably transparent or optically clear such as to allow optical examination and measurement. The two dimensional array of analysis chambers, and optionally the branching pattern of entry channels coupled to each of the analysis chambers in the array to enable the analysis chambers to be filled in parallel, are preferably made of a polymeric material especially a plastic material. In preferred embodiments the analysis chambers, each having a substantially planar shape, have a height defined by a lower part into which the chambers have been formed and a cover part which forms the top of the chambers. The cover part is preferably more flexible than the lower part so that attachment of the cover part to the lower part, e.g. by gluing, welding, especially sonic welding, solvent bonding, melting etc. does not alter the dimensions especially the flatness of the floor of the chambers formed in the lower part.

The size of the individual analysis chambers can be between 0.02 and 500 mm$^2$. The height of the analysis chambers can be between 1 and 10 μm. The height of the analysis chamber depends on which cells or parasites are to be analyzed. For red blood cells the preferred height is between 2 and 4 micrometer, and more preferably 3 micrometer. Smaller gap height will remove all normal blood cells and gives pure blood plasma. Larger gap height will lead to mixtures of red blood cells and for example parasites.

The entry and exit channels can have a depth of 10-200 μm and a width of 50-1000 μm. Another aspect of the invention provides a method of preparing thin layers of a fluid sample or for preparing layers of a fluid containing cells, especially red blood cells, each layer having a monolayer of cells, especially red blood cells, for analysis, using apparatus having a two dimensional array of analysis chambers, and a branching pattern of entry channels coupled to each of the analysis chambers in the array to enable the analysis chambers to be filled in parallel, the analysis chambers each having a substantially planar shape having a height less than that of the entry channels so as to produce the thin layers or the layers of the fluid containing cells, especially red blood cells, each layer having a monolayer of cells, especially red blood cells when the chambers are filled with the fluid sample, the method having the steps of providing the fluid sample, and supplying it to the pattern of entry channels, to cause the fluid sample to fill the analysis chambers. The filling is preferably by capillary action. In embodiments of the present invention, filling by capillary action can be defined by capillary filling by a standard aqueous solution such as PBS or optionally pure water. This means that filling by capillary action in accordance with the present invention, means filling by capillary action using PBS (Phosphate buffered saline) as a standard, (or optionally pure water) e.g. at standard temperature and pressure. PBS is a salty buffer solution containing sodium chloride, sodium phosphate and (in some formulations) potassium chloride and potassium phosphate. The osmolarity and ion concentrations of the solution usually match those of the human body. One way of making PBS includes dissolving 800 g NaCl, 20 g KCl, 144 g Na$_2$HPO$_4$.12H$_2$O and 24 g KH$_2$PO$_4$ in 8 L of distilled water, and topping up to 10 L. The pH is about 6.8, but when diluted to 1×PBS it should change to 7.4. On dilution, the resultant 1×PBS should have a final concentration of 137 mM NaCl, 10 mM Phosphate, 2.7 mM KCl, and a pH of 7.4. Another preparation is described by Sambrook, Fritsch and Maniatis, (1989) in Molecular Cloning: A Laboratory Manual, 2nd ed., Cold Spring Harbor Laboratory Press, Cold Spring Harbor, N.Y., volume 3, appendix B.12: dissolve in 800 ml of distilled H$_2$O, 8 g of NaCl, 0.2 g of KCl, 1.44 g of Na$_2$HPO$_4$.12H$_2$O and, 0.24 g of KH$_2$PO$_4$. Adjust the pH to 7.4 with HCl and add H$_2$O to 1 liter.

Capillary action according to some methods of the present invention makes use of chambers and/or channels having dimensions capable of filling with any one of the PBS preparations mentioned above, e.g. at standard temperature and pressure or optionally pure water at standard temperature and pressure.

Methods of the present invention preferably use a high number of chambers combined with the use of comb-like or fractal filling and venting channels. Devices according to embodiments of the present invention can have a large number of chambers. In a preferred embodiment the total surface will be 20 mm$^2$ and the field of view 0.2×0.2=0.04 mm$^2$, which means 500 reaction chambers. A number of chambers for any of the embodiments of the present invention can be between 100 and 1000 chambers.

Methods of the present invention can be used with apparatus that has a pattern of exit channels with one or more exit channels coupled to each of the analysis chambers. The patterns of the entry and exit channels can each comprise a comb pattern, fingers of the comb patterns being interdigitated, and the analysis chambers being arranged between the interdigitated fingers of the comb patterns. Another aspect of the present invention is a method step of fluidic stopping of the sample fluid at or adjacent to the exit channels or vents. By introducing sharp transitions in the channel wall such as to change the width of the channel in all directions, the contact line of the liquid and the wall becomes frustrated since the angle cannot be changed abruptly. This leads to a hesitation of the fluid followed by so-called contact line pinning. The meniscus becomes frozen at the surface. If the channel is quadratic and has 4 walls then the widening is done at all 4 walls at the same spot the pinning can be very stable. The wall transitions preferably increase the angle count, i.e. they can be preferably stepwise expansions. With fluids like blood evaporation of water can lead to permanent pinning by vitrification of the liquid at the meniscus.

Another aspect of the invention provides a corresponding method of manufacturing such apparatus.

Another aspect of the invention provides an analysis system comprising an optical detector for analysing thin layers of a fluid sample, or for analysing layers of a fluid containing cells, especially red blood cells, each layer having a monolayer of cells, and apparatus for producing the thin layers of the fluid sample or the layers of the fluid containing cells, especially red blood cells, each layer having a monolayer of cells, the apparatus having a two dimensional array of analysis chambers, and a branching pattern of entry channels coupled to each of the analysis chambers in the array to enable the analysis chambers to be filled in parallel, the analysis chambers each having a substantially planar shape having a height less than that of the entry channels so as to produce the thin layers or the layers of the fluid containing cells, especially red blood cells, each layer having a monolayer of cells, when the chambers are filled with the fluid sample.

Another aspect of the invention provides a method of analyzing thin layers of a fluid sample or of analysing layers of a fluid containing cells, especially red blood cells, each layer having a monolayer of cells, prepared using an apparatus having a two dimensional array of analysis chambers, and a branching pattern of entry channels coupled to each of the analysis chambers in the array to enable the analysis chambers to be filled in parallel, the analysis chambers each having a substantially planar shape having a height less than that of the entry channels so as to produce the thin layers or the layers of a fluid containing cells, especially red blood cells, each layer having a monolayer of cells, when the chambers are filled with the fluid sample, the method having the steps of providing an optical detector and using the optical detector to analyze the thin layers or the layers of a fluid containing cells, especially red blood cells, each layer having a monolayer of cells, in the analysis chambers.

Any of the additional features can be combined together and combined with any of the aspects. Other advantages will be apparent to those skilled in the art, especially over the prior art. For example the present invention does not use a single chamber, but an array of chambers coupled in parallel. The array can be a two-dimensional array that therefore allows a compact design. The two dimensional array of chambers are fluidly coupled to enable them to be filled in parallel. In particular the devices of the present invention have multiple analysis chambers, the chambers having a height less, e.g. substantially less than that of entry channels.

Numerous variations and modifications can be made without departing from the claims of the present invention. Therefore, it should be clearly understood that the form of the present invention is illustrative only and is not intended to limit the scope of the present invention.

BRIEF DESCRIPTION OF THE DRAWINGS

How the present invention may be put into effect will now be described by way of example with reference to the appended drawings, in which.

DETAILED DESCRIPTION OF THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

The term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

The present invention relates to apparatus and methods for automated analysis of samples in, for example, a cartridge. For automated analysis of samples in a cartridge, accurate control of the layer thickness of the fluid sample can be important. At least some of the embodiments involve thin cell smear preparation and a design of a new cartridge made in plastic. Cell smear preparation preferably means forming layers of a fluid containing cells, especially red blood cells, each layer having a monolayer of cells. The cells are preferably non-overlapping. The cells are preferably red blood cells. It can be applied advantageously for analysis systems for medical diagnostics of blood-born diseases such as parasites of which malaria microscopy diagnosis is one example. As red blood cells do not contain DNA, the presence of foreign cells in the blood can be determined by any method, e.g. any optical method, e.g. any staining method which demonstrates the presence of DNA. An advantage of the present invention, for example, can be lower cost and/or faster operation for a given performance and/or provision of large areas for analysis.

Low cost components such as those of moulded plastic usually lack the required flatness to achieve a constant channel height over large areas. As will be described in more detail below, a microstructure which can be fabricated with low cost in plastic can provide a more precise layer thickness in the micrometer regime with little susceptibility to user influence. In some embodiments of the invention, an array of areas with narrow gaps is created connected by channels with larger gaps. The area size and aspect ratio can in some cases be adjusted to the image analysis requirements. Individual areas are substantially smaller than the total area to be analyzed. In this way the fast and well controlled creation of mono layers of cells can be enabled.

By way of introduction to the embodiments, some problems or disadvantages addressed by some embodiments of the invention will be described briefly:

In order to create a thin smear of blood (e.g. a monolayer of cells especially a monolayer of red blood cells, especially a layer of non-overlapping red blood cells), one needs to spread the sample over a large surface area. However, in this context designing a closed cartridge, and moreover one in plastic (to keep costs low), poses different technical challenges. The cartridge can be a disposable cartridge. A cartridge is a device which can be fitted into, e.g. slotted into a measurement apparatus, to allow analysis of the contents of the cartridge. For example, the flow resistance presented by a small gap (bottom-top distance in cartridge in the order of the thin height of the smear) makes it harder to fill the analysis area quickly with a fluid sample over a large area. Also, there may be large process variations causing variation in gap size when fabricating such a thin gap in plastic over a large surface area as will now be explained in more detail:

Capillary filling of large areas with narrow gaps is limited by the flow resistance of the fluid inside the channel $$\left(\Delta p_v = \frac{12\eta L V}{h^2}\right),$$

where the pressure drop is $\Delta p_v$, length of channel is L, average flow speed is V, height of the channel h. With a channel height, h, of the order of the thickness of the cells the cells created a strong resistance to flow. This means that the distances that can be overcome are limited.

The flow speed and the distance which can be filled depends on the viscosity of the fluid, $\eta$, which in the case of blood can vary in a broad range, mainly depending on the hematocrit value (concentration of red blood cells).

The capillary force scales with the inverse of the gap height ($\Delta p_c = 2\sigma \cos \Theta/h$) where $\Delta p_c$ is the capillary force, surface tension is given by $\sigma$, contact angle of fluid to substrate is $\Theta$, height of the gap is h.

Small thickness variations lead to strong flow speed variations and consequently unpredictable filling patterns, incomplete filling and air inclusions.

For low cost cartridges the substrate and cover need to be made from plastic which is either processed by extrusion (foil) or injection moulding (thicker parts and frame). Injection moulding leads to shape deviations due to inhomogeneous cooling inherent to the process. This leads to flatness deviations of the order of tens of microns locally and much more overall. Foils can be processed with tight thickness tolerances and flatness, however, the bending stiffness is very low (scales with $1/d^3$) so that large variations in the gap can be expected which lead to inhomogeneous and non-reproducible filling and may lead to too large gaps which induces cell stacking and compromises image analysis. This is very important as variations in effective optical thickness of stain leads to variations in image analysis (thresholds, etc.) and hence to false negatives or positives.

For all these reasons it is difficult to produce low cost cartridges for thin smear preparation of fluid samples such as blood, with the desired precision of layer thickness, for use in imaging based malaria diagnosis for example.

Figure 1:
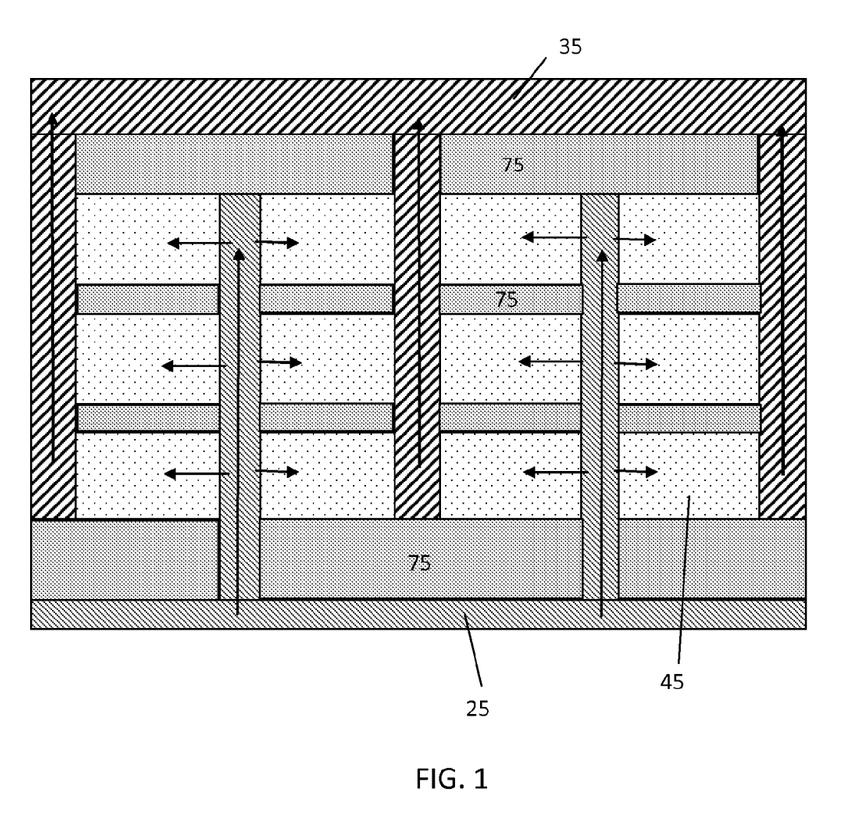
FIG. 1 is a plan view of part of a cartridge showing an array of analysis areas and a repetitive interdigitated channel structure.

FIG. 1, plan view of cartridge according to a first embodiment:

Some embodiments of the present invention have analysis areas in the form of an array of microfluidic chambers. This can enable more spacers for a given overall area, and thus help maintain a specified height. These chambers can be coupled in parallel by entry channels, so as to enable rapid filling. A single sampling port can be arranged fluidly connected to the entry channels to allow easy entry of a fluid sample. Venting channels are also arranged. The channels can be in an interdigitated pattern so as to enable more rapid filling of many chambers in parallel. In some cases there is a set of interdigitated fingers for capillary flow of the sample towards the array of analysis areas. The filling is preferably by capillary action. In embodiments of the present invention, filling by capillary action can be defined by capillary filling by a standard aqueous solution such as PBS, e.g. at standard temperature and pressure or optionally by pure water at standard temperature and pressure. PBS is a salty buffer solution containing sodium chloride, sodium phosphate and (in some formulations) potassium chloride and potassium phosphate. The osmolarity and ion concentrations of the solution usually match those of the human body. One way of making PBS includes dissolving 800 g NaCl, 20 g KCl, 144 g $Na_2HPO_4.12H_2O$ and 24 g $KH_2PO_4$ in 8 L of distilled water, and topping up to 10 L. The pH is about 6.8, but when diluted to 1×PBS it should change to 7.4. On dilution, the resultant 1×PBS should have a final concentration of 137 mM NaCl, 10 mM Phosphate, 2.7 mM KCl, and a pH of 7.4. Another preparation is described by Sambrook, Fritsch and Maniatis, (1989) in Molecular Cloning: A Laboratory Manual, 2nd ed., Cold Spring Harbor Laboratory Press, Cold Spring Harbor, N.Y., volume 3, appendix B.12: dissolve in 800 ml of distilled $H_2O$, 8 g of NaCl, 0.2 g of KCl, 1.44 g of $Na_2HPO_4.12H_2O$ and, 0.24 g of $KH_2PO_4$. Adjust the pH to 7.4 with HCl and add $H_2O$ to 1 liter.

Capillary action may be defined by filling by capillary forces when using any one of the above PBS solutions, e.g. at standard temperature and pressure or optionally with pure water at standard temperature and pressure.

To create an automatic readable monolayer of red blood cells from a certain amount of whole blood, the format and configuration of the entry canals and analysis chambers are essential. Entry canals and the entrance of analysis chambers are easily clogged by large white blood cells. The total entrance width of all analysis chambers must be so large that it minimizes this. For the analysis of one microliter of whole blood, the minimal total width of the analysis chamber entrance is at least 110 mm (the number of white blood cells in one microliter times the diameter=$1.1\ 10^4 * 10\ 10^{-6}$ m=110 mm).

The inner surfaces of the entry channels and chambers are preferably hydrophilic. This can be achieved by selection of the materials from which the device is made or by processes such as plasma or corona treatment or by coating with a hydrophilic coating.

There can be another set of interdigitated hollow fingers for venting channels. Venting channels are preferably adapted so that they form liquid stops but allow gas to flow through not prevent or at least cause hesitation of liquid flow. E.g. the surface of the venting channels may be hydrophobic or the venting channel width may change abruptly wider such as to pin the fluid sample. The analysis areas can be located between the fingers mentioned above. The analysis areas can be arranged to have dimensions comparable to a field of view of a microscope of an analysis system.

Figure 2:
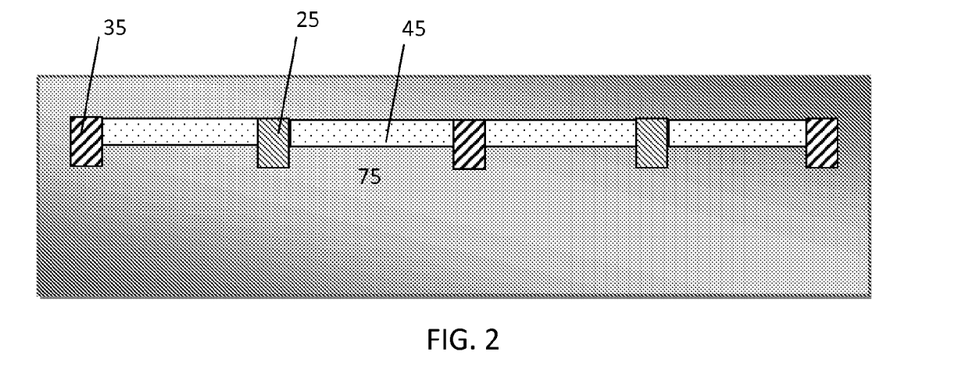
FIG. 2 is a cross-section view of the cartridge.

In FIG. 1 a top view of an example of the apparatus in the form of a cartridge is shown and in FIG. 2 is a cross-section view of the same example. Notably the overall analysis area as shown in FIG. 1 is divided into small elementary analysis areas such that the plastic cartridge has an array of small analysis areas each having a height (gap) substantially equal to the desired height of the thin smear (of the order of µms). In some cases the small analysis area corresponds to the field of view of an optical detector such as a microscope used in the system. Such division solves notably the problem of plastic process variation during fabrication. At least one of the materials above or below the analysis chambers is preferably transparent or optically clear to allow optical examination methods.

FIG. 1 also shows sealing areas 75 notably between analysis areas as will be described more in details after.

FIG. 1 also shows a specific arrangement of entry channel in the form of filling channel 25, exit channel in the form of venting channel 35 and substantially planar analysis chamber in the form of analysis area 45: There is a flow communication between entry channels, small analysis areas and exit channel (venting channel for example), the height of entry channel being substantially larger than that of small analysis areas (flow is fine because the gap of the entry channel is thicker, and because, despite the thin gap of the analysis area its cross sectional area is small). Optionally, there can be a single sample port for entry of fluid, the sample port being fluidly connected to the entry channels. A typical flow of the fluid in the cartridge is illustrated in FIG. 1 by the different arrows.

In another embodiment, the venting channel (for air pressure control) comprises means for substantially retaining the blood into the small analysis areas (for example, use of a small step at the interface of the venting channel and each analysis area). Another aspect of the present invention is the introduction of fluidic stops at or adjacent to the exit channels or vents.

Figure 3:
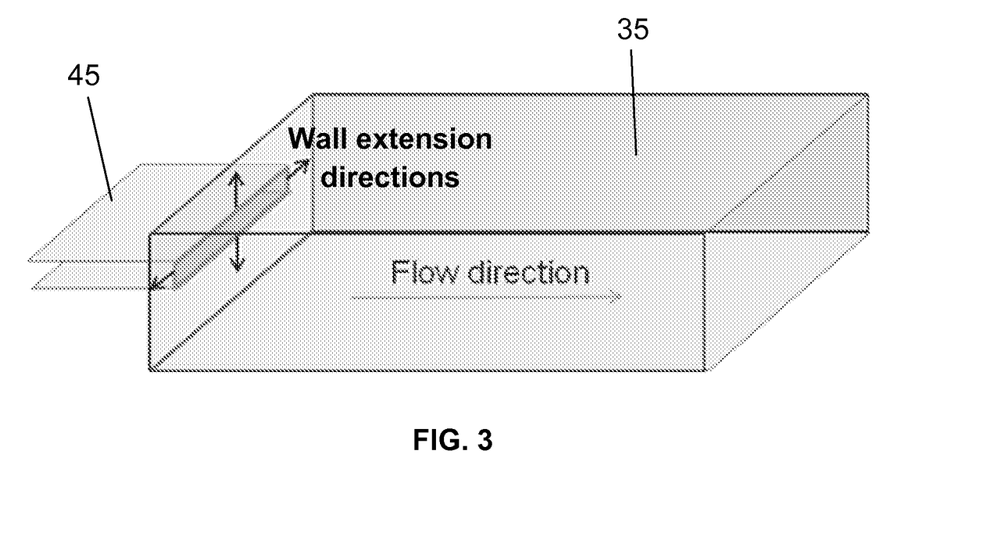
FIG. 3 is a zoom in view in perspective a transition between an analysis area and a venting channel according tone embodiment of the invention.

By introducing sharp transitions in the channel wall such as to change the width of the channel in all directions as shown notably by arrows in FIG. 3, the contact line of the liquid and the wall becomes frustrated since the angle cannot be changed abruptly. This leads to a hesitation of the fluid followed by so-called contact line pinning. The meniscus becomes frozen at the surface. If the channel is quadratic and has 4 walls then the widening is done at all 4 walls at the same spot the pinning can be very stable. The wall transitions preferably increase the angle count, i.e. they can be preferably stepwise expansions. With fluids like blood evaporation of water can lead to permanent pinning by vitrification of the liquid at the meniscus.

It is to be noted that in certain cases, a sudden widening in two directions, instead of the four as mentioned above can be sufficient for pinning stability. This notably may depend on how strongly wetting the surfaces are for the liquid.

The cartridge can be designed for fast and reproducible filling with the fluid sample such as blood, to obtain a monolayer of red blood cells for example, with a tight layer thickness tolerance. The embodiment of FIG. 1 has a tree type pattern of interdigitated entry and venting channels coupled to the analysis areas. These areas have the required gap height and are separated by spacers, which help to control the flow direction as well as setting the gap height. The analysis areas can be arranged to match the optical field of the image analysis equipment and have a maximum width to limit the gap variation. The spacers are formed as an integral part of a substrate which can be produced by replication from a master with the inverse structure. The cover of the cartridge can be made from a flat thin sheet of plastic or glass for example, which can be coated on the inner surface with one or many types of reagents if desired, depending on the type of analysis being used. The substrate and cover can be joined for instance by laser or thermal bonding. Preferably the cartridge is made of an upper cover part and a lower part. The channels and analysis chambers can be formed in the lower part and a cover part is sealed to the top, e.g. by gluing, welding, sonic welding, laser welding, thermal bonding etc. The cover part is preferably more flexible than the lower part so that the dimensional stability and the flatness of the analysis chambers in the lower part is not affected by the connection to the upper part. For the same reason it is preferred if the cover and the lower part of similar thermal expansion coefficients, e.g. less than 25%, more preferably less than 10% difference so that the height of the chambers does not change with temperature changes due to sagging of the cover part into the analysis chambers.

The entry channel is branched and has a larger channel height than the analysis area. The entry channel can be connected to a single sample entry port. The flow resistance is low to enable fast filling of the analysis areas such that the filling of the analysis areas starts almost simultaneously. The flow path in the analysis areas can have a narrow gap such as 5 µm and is preferably short which assures complete and fast filling up to the venting channel. The venting channel is connected to a single exit (waste chamber). Due to the step in height at the transition from the analysis to the vent area the blood will stop there as the capillary action will reduce, and the venting channel will not fill (at least not until all analysis areas are filled).

The dimension of the analysis area can be related to the field of the imaging optics (e.g. such that at least one edge is inside the field). Devices of the present invention preferably have a high number of chambers combined with the use of comb-like or fractal filling and venting channels. Devices according to embodiments of the present invention have a large number of chambers. In a preferred embodiment the total surface will be 20 mm$^2$ and the field of view 0.2× 0.2=0.04 mm$^2$, which means 500 reaction chambers. A number of chambers for any of the embodiments of the present invention can be between 100 and 1000 chambers.

The apparatus has a pattern of exit channels with one or more exit channels coupled to each of the analysis chambers. The patterns of the entry and exit channels can each comprise a comb pattern, fingers of the comb patterns being interdigitated, and the analysis chambers being arranged between the interdigitated fingers of the comb patterns.

The analysis system can have imaging optics and image analysis software which can recognize the orientation of the analysis area and use that as control input for a stepping control to control the relative movement of the cartridge and imaging approach during analysis. Features can be added to the walls which separate the analysis areas or alternatively features can be present inside the analysis area to provide information about the position of the analysis area with respect to the total cartridge. This can be a code or symbol which is interpreted by the image analysis software.

FIG. 2, cross section view

The substrate surface which defines the channels can have at least three different levels: (i) the level of the entry channels for the fluid sample, (ii) the level of the analysis areas, and (iii) the sealing area for the spacers between the analysis areas.

The venting area can have the same level as the inlet or a level between that of the inlet and that of the analysis area.

The area of the inlet can be represented as a kind of a comb structure which is interdigitated with the venting structure such that a multitude of equal analysis areas are defined as connections between the two. FIG. 1 represents only a small part to illustrate the interdigitated arrangement. It is only an indication. More channel splitting can be designed in a kind of fractal structure to efficiently cover the total surface area. The analysis areas are separated by sealing areas. The step height between the analysis and the sealing area defines the gap height of the analysis area. The size of the individual analysis areas can be preferably between 0.01 and 1 mm$^2$, more preferably between 0.03 and 0.2 mm$^2$. The gap height in the analysis area can be between 1 and 10 µm, more preferably between 3 and 6 µm. The total analysis area is preferably between 1 and 500 mm$^2$, more preferably between 5 and 250 mm$^2$.

The sealing areas have a width of preferably between 50 and 500 µm.

The filling and venting channels have a depth of preferably 10-200 µm, more preferably 50-100 µm and a width of 50-1000 µm, more preferably 100-300 µm.

Materials which can be used for the substrate as well as the cover are preferably polymers, e.g. transparent especially optically clear polymers, like polymethylmethacrylate, polystyrene, polycarbonate, cyclo-olefin(co)polymer, polyesters, polyurethanes, etc. Entry channels can be treated to reduce the contact angle to increase the capillary filling forces, analysis areas can be pretreated to enhance cell sticking and/or cell staining. Such treating can be plasma or corona discharge or coating with a hydrophilic coating. On the other hand, an aspect of the present invention is the introduction of fluidic stops to prevent liquid from discharging through the venting channels while allowing gas to vent. Venting channels can be pretreated to increase the contact angle, preferably to more than 90 deg to avoid wetting by the fluid sample. Such treating can be a coating with a hydrophobic coating. Another method is increasing the width of the exit channel in all directions abruptly in order to pin the meniscus of the fluid sample.

Cover and substrate can be joined permanently by a bonding technology, like laser welding or other, or alternatively just be in contact with each without permanent bonding. Contact areas can be pretreated to enhance the sticking of the cover to the substrate. Preferably the cover is more flexible than the substrate so that when joined the dimensions and flatness of the substrate is not affected.

The entrance region for filling the blood can be designed such that convenient filling is enabled, e.g. by providing a sample port such as a through hole and optionally a cap which can be closed after filling. Reagents can be provided in dry form in the entrance region. At the end of the venting channel a waste reservoir can be included to avoid possible spilling of excess of fluid such as blood.

Figure 5:
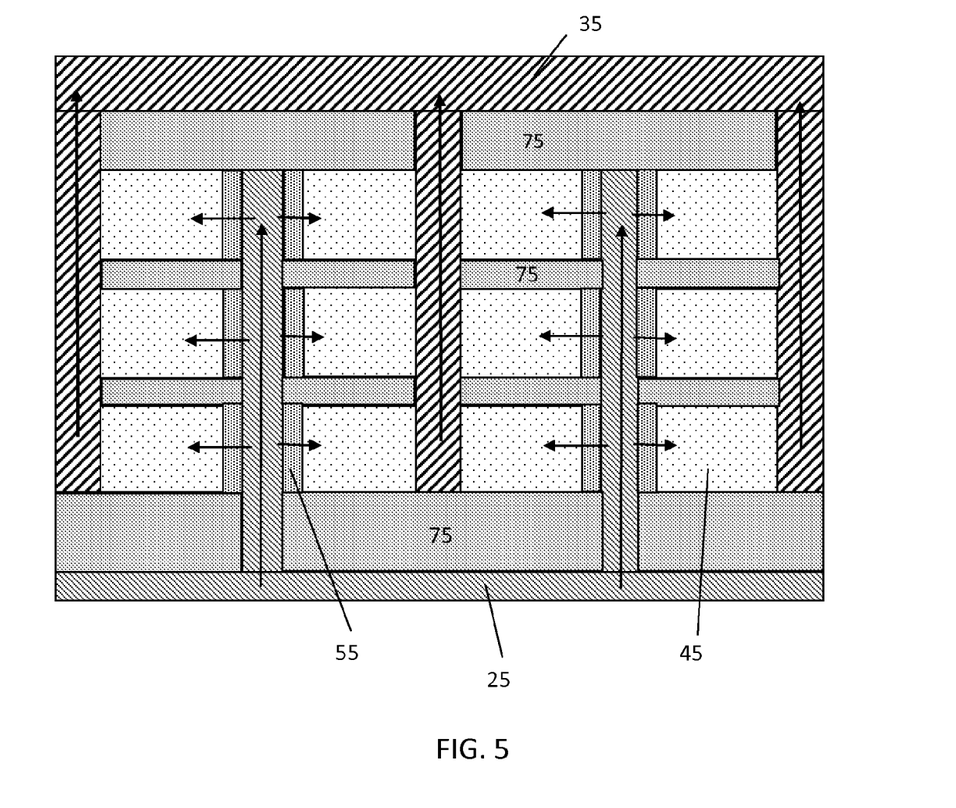
FIG. 5 shows a plan view of part of a cartridge according to the invention showing including additional analysis areas for red blood cells infected with mature parasites FIG. 6. is a cross-section view of the cartridge according to FIG. 5.
Figure 6:
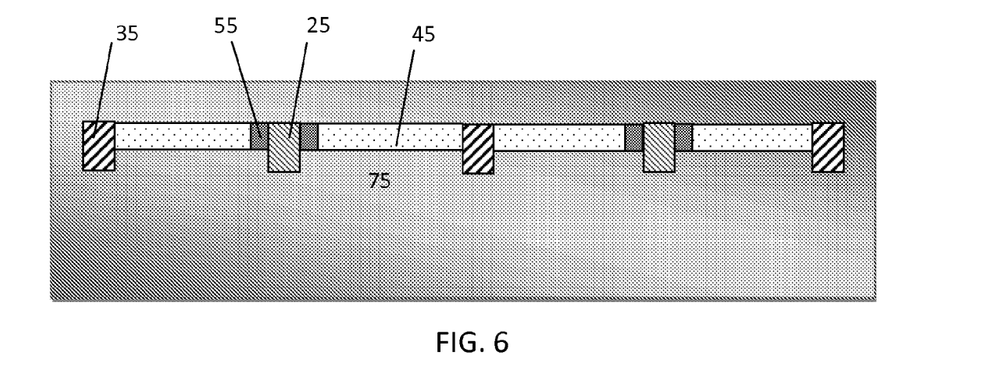

FIGS. 5 and 6 show a cartridge according to the invention, comprising an additional zone (55) between the entry channels (25) and analysis chambers (45), wherein the height of this zone is less than the entry channels (25) and more than the analysis chambers (45). The height of the additional zone (55) preferably is below 6 micron. This additional area has several advantages. To speed up the detection of malaria parasites in blood, this additional area in the cartridge is created in which mature malaria parasites are enriched.

As a specific example, red blood cells with mature parasite cannot enter an analysis chamber smaller than 3 micron while they easily flow into a 4 micron area. The difference is small but easily made by etching an additional scan area, see schematic view in FIGS. 5 and 6. This additional area is advantageous, as otherwise the white blood cells also will concentrated at the rim of the scan area and obscure the mature parasites. White blood cells are too large to enter a 4 micron gap so only thick red blood cells with mature parasite will be enriched in this area.

In a preferred embodiment, add a larger blood volume chamber is added to the cartridge to quickly store blood from a finger prick. If this chamber is filled, sufficient blood is taken from the finger prick to ensure a reliable measurement. The larger volume chamber can also be additional channels on the cartridge.

In general, dyes can be added to the analysis chambers by pre-filling them with a dye solution, e.g. in organic solvents. These solvents quickly evaporate and leave the necessary amount of dried dye in the analysis chambers. The dye will be (re)dissolved by the entering biological liquid, preferably blood.

Manufacturing steps for the cartridge:

The structured substrates can be manufactured by injection molding or other replication technology. The master structure which is required as a mold can be produced with the aid of photolithography; electroplating and/or etching. One suitable method requires two lithographic masks. The first one contains a pattern for the analysis areas. In a second step a mask representing the channel structure of the entry and venting channels is used in order to create a resist pattern for the selective etching of the substrate (e.g. silica). After etching the etch resist is stripped and the photopolymer on the analysis areas remains on the substrate. In this way three levels can be created on the substrate. An alternative method is to use multi-layer resists such as SU-8. This substrate can then by copied into a metal, e.g. Ni shim by electroplating in a way which is well established for instance in optical disc manufacturing (e.g. DVD, CD-Rom discs). The metal, e.g. Ni shim is then used as an insert in the mold for replication in plastic by molding. The replication method can include manufacturing the lower part or substrate by a replication method using a master followed by attaching the cover layer by any suitable method, e.g. welding, sonic welding, laser welding, gluing, thermal bonding etc.

FIG. 3, Analysis system

Figure 4:
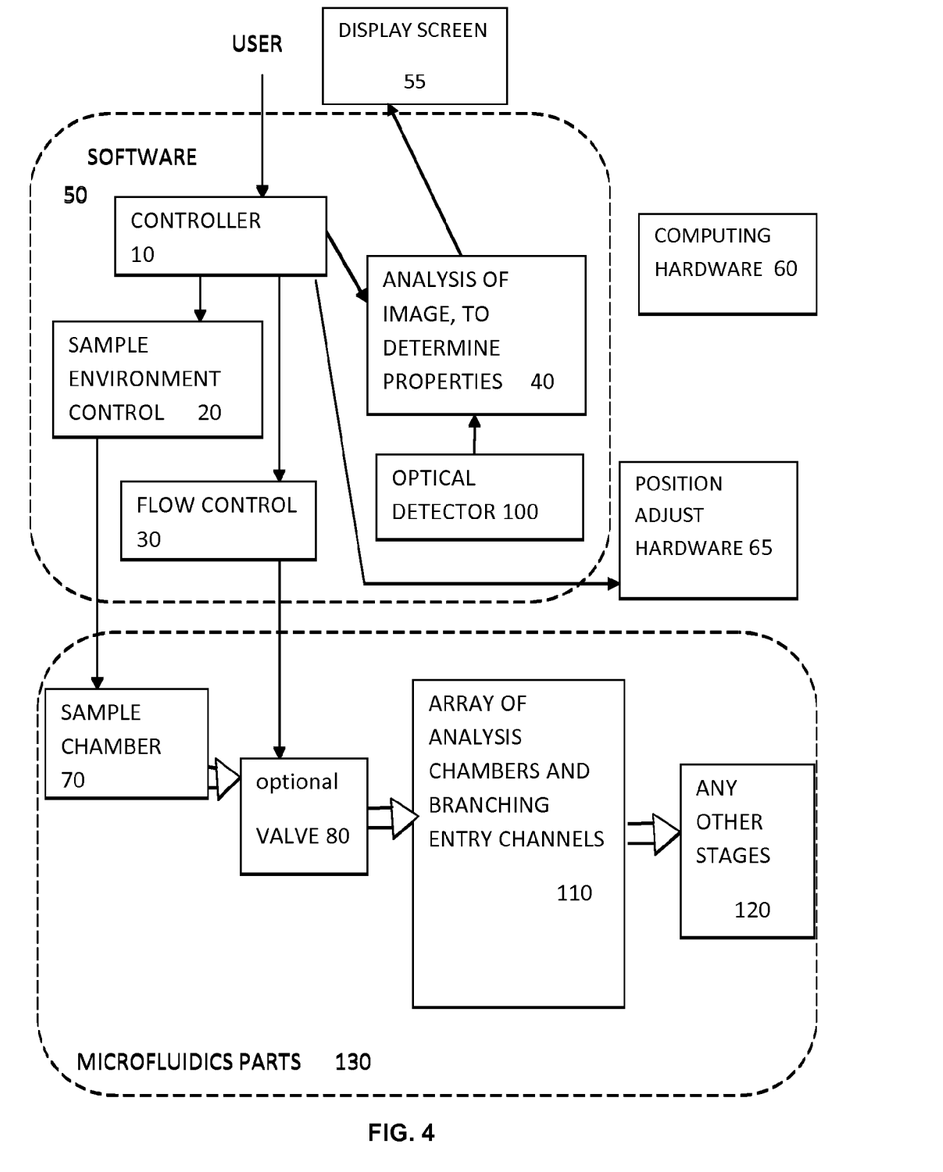
FIG. 4 shows a schematic view of an analysis system including the cartridge.

FIG. 4 shows an analysis system including the apparatus described above. Microfluidics parts 130 are shown at a lower half of the view, and software 50 and computing hardware 60 shown in an upper half. The microfluidics parts can be in the form of a removable cartridge, or can be incorporated in the system if they can be washed out between uses. This system has at least a sample chamber 70 for controlling admission to the branching entry channels and analysis chambers 110. If required optional items such as valves 80 or actuators such as pumps may be provided however fluid entry into the analysis chambers is preferably by capillary action. Any other stages 120 can be included after the exit channels of the analysis areas, depending on the application. There can be many analysis areas for doing many evaluations in parallel as desired. One or more evaluations can be made, e.g. several chambers may be dedicated to one evaluation, all the chambers may be dedicated to one evaluation or many evaluations can be made in parallel. Suitable reactants may be pre-installed in the analysis chambers, e.g. suitable stains. An optical detector 100 views the analysis chambers and feeds an image signal to a part 40 in the software 50 for analysis of the image to determine the properties of the sample, for presentation to a user typically through a display screen 55.

The software parts also include a controller 10 for controlling the analysis part 40 and controlling a flow control part 30. The flow control part controls the valves or pumps to control the supply of the samples. Optionally the controller may be coupled to a position adjuster 65 for moving the relative position of the cartridge and the detector. Optionally the controller can be coupled to an environment controller 20 for the samples. Further parts of the software can be arranged to provide a user interface and further analysis of the results. All the software can use conventional programming languages and can be run on conventional computing hardware 60 such as a general purpose microprocessor, a personal computer or other hardware.

The controller may be any suitable controller or microcontroller, e.g. may include a microprocessor or a programmable logic device such as an FPGA.

EXAMPLE

A device according to the present invention is described in the present example. The device can comprise one entry channel with a length of 55 mm and two analysis chambers of 55 mm width and 4 mm length alongside this channel. A second envisioned and more compact approach is to have two or three entry channels of 28 mm long and four analysis chambers. Each chamber has a 28 mm width entrance and is 4 mm long. Filling time depends on the filling characteristics of the entry channels and the length of the channel that is supplying the blood to the entry channels. An analysis chamber with these large entrance widths and only a length of 4 mm fills very fast, less than few seconds. The necessary time to fill the entry channel of 1 mm width, 28 mm long and a gap 18 micrometer with only capillary forces and a supply channel of 30 mm is 13 sec which fulfill the requirement of a filling time lower that 1 minute. It is most beneficial to have all entry channels to be as small as possible as this minimize the total amount of blood that is needed from the finger prick.

Experiments with prototypes show that devices according to the present invention fill within 40 seconds with whole blood.

Applications:

Applications can include at least cell-based diagnostics, such as malaria diagnosis, HIV, HCV, FBC, and so on. By cell-based is meant that cells are in the fluid sample. However, for none of the methods of the embodiments of the present invention is the diagnostic method restricted to identifying aspects of the cells as a part of the diagnostic method. For example red blood cells do not contain DNA or RNA, and hence detecting either DNA or RNA in a blood sample is a diagnostic test in accordance with the present invention as detecting DNA or RNA indicates that there ca be foreign material in the blood sample. The apparatus can be in the form of cartridges for rapid distributed testing. The apparatus can form part of a biosensor, or any other type of medical diagnostic device. Other applications, variations and additions can be envisaged within the claims.

The invention claimed is:

1. Apparatus for producing layers of a fluid containing cells, each layer having a monolayer of cells for analysis, the apparatus having a two dimensional array of analysis chambers, and a branching pattern of entry channels coupled to each of the analysis chambers in the array to enable the analysis chambers to be filled in parallel, the analysis chambers each having a substantially planar shape having a height less than that of the entry channels so as to produce the layers of a fluid containing cells, each layer having a monolayer of cells when the chambers are filled with the fluid sample, the apparatus further comprising an additional zone between the entry channels and analysis chambers, wherein the height of this zone is less than the entry channels and more than the analysis chambers.

2. The apparatus of claim 1 wherein the height of the additional zone is below 6 micron.

3. The apparatus of claim 1 having a pattern of exit channels coupled to the array of analysis chambers.

4. The apparatus of claim 2 further comprising liquid stops to stop flow of liquid through the exit channels but to allow gas to pass.

5. The apparatus of claim 2, the patterns of the entry and exit channels each comprising a comb pattern, fingers of the comb patterns being interdigitated, and the analysis chambers being arranged between the interdigitated fingers of the comb patterns.

6. An apparatus for producing layers of a fluid containing cells, each layer having a monolayer of cells for analysis, the apparatus having a two dimensional array of analysis chambers, and a branching pattern of entry channels coupled to each of the analysis chambers in the array to enable the analysis chambers to be filled in parallel, the analysis chambers each having a substantially planar shape having a height less than that of the entry channels so as to produce the layers of a fluid containing cells, each layer having a monolayer of cells when the chambers are filled with the fluid sample;
wherein the total area of each of the analysis chambers is between 100 and 2000 mm$^2$ and/or the height of the analysis chambers is between 1 and 10 μm, and
the entry channels have a depth of 10-200 μm and a width of 50-1000 μm.

7. A method of preparing layers of a fluid containing cells, each layer having a monolayer of cells, for analysis, using apparatus having a two dimensional array of analysis chambers, and a branching pattern of entry channels coupled to each of the analysis chambers in the array to enable the analysis chambers to be filled in parallel, the analysis chambers each having a substantially planar shape having a height less than that of the entry channels so as to produce the layers of the fluid containing cells, each layer having a monolayer of cells, when the chambers are filled with the fluid sample, the method having the steps of providing the fluid sample, and supplying it to the pattern of entry channels, to cause the fluid sample to fill the analysis chambers, the apparatus further comprising an additional zone between the entry channels and analysis chambers, wherein the height of this zone is less than the entry channels and more than the analysis chambers.

8. A method of manufacturing apparatus for producing layers of a fluid containing cells, each layer having a monolayer of cells, for analysis, the method having the steps of forming a two dimensional array of analysis chambers, and forming a branching pattern of entry channels coupled to each of the analysis chambers in the array to enable the analysis chambers to be filled in parallel, the analysis chambers being formed so as to have a substantially planar shape having a height less that of the entry channels, wherein the total area of each of the analysis chambers is between 100 and 2000 mm$^2$ and/or the height of the analysis chambers is between 1 and 10 μm, and the entry channels have a depth of 10-200 μm and a width of 50-1000 μm.

9. An analysis system comprising an optical detector for analyzing layers of a fluid containing cells, each layer having a monolayer of cells, and apparatus for producing the layers of a fluid containing cells, each layer having a monolayer of cells, the apparatus having a two dimensional array of analysis chambers, and a branching pattern of entry channels coupled to each of the analysis chambers in the array to enable the analysis chambers to be filled in parallel, the analysis chambers each having a substantially planar shape having a height less than that of the entry channels so as to produce the layers of a fluid containing cells, each layer having a monolayer cells, when the chambers are filled with the fluid sample, wherein the total area of each of the analysis chambers is between 100 and 2000 mm$^2$ and/or the height of the analysis chambers is between 1 and 10 μm, and the entry channels have a depth of 10-200 μm and a width of 50-1000 μm.

10. The system of claim 9 having a pattern of exit channels coupled to the array of analysis chambers.

11. The system of claim 10, the patterns of the entry and exit channels each comprising a comb pattern, fingers of the comb patterns being interdigitated, and the analysis chambers being arranged between the interdigitated fingers of the comb patterns.

12. A method of analyzing layers of a fluid containing cells, each layer having a monolayer of cells, prepared using an apparatus having a two dimensional array of analysis chambers, and a branching pattern of entry channels coupled to each of the analysis chambers in the array to enable the analysis chambers to be filled in parallel, the analysis chambers each having a substantially planar shape having a height less than that of the entry channels so as to produce the layers of a fluid containing cells, each layer having a monolayer of cells, when the chambers are filled with the fluid sample, wherein the total area of each of the analysis chambers is between 100 and 2000 mm$^2$ and/or the height of the analysis chambers is between 1 and 10 μm, and the entry channels have a depth of 10-200 μm and a width of 50-1000 μm, the method having the steps of providing an optical detector) and using the optical detector to analyze the layers of a fluid containing cells, each layer having a monolayer of cells, in the analysis chambers.

\* \* \* \* \*